United States Patent [19]

Kinoshita et al.

[11] Patent Number: 5,718,097
[45] Date of Patent: Feb. 17, 1998

[54] SAMPLE CONTAINER SEALER HAVING FUNCTION OF SETTING LOAD

[75] Inventors: Ryoichi Kinoshita; Keiko Ohshiro, both of Chiba, Japan

[73] Assignee: Seiko Instruments Inc., Chiba, Japan

[21] Appl. No.: 688,497

[22] Filed: Jul. 30, 1996

[51] Int. Cl.[6] .............................. B65B 7/28; B65B 51/00
[52] U.S. Cl. ........................... 53/75; 53/201; 53/366
[58] Field of Search ................................. 53/486, 75, 76, 53/366, 201, 289

[56] References Cited

U.S. PATENT DOCUMENTS

| | | | |
|---|---|---|---|
| 3,972,758 | 8/1976 | Bieber | 53/486 |
| 4,136,443 | 1/1979 | Nabiullin et al. | 53/366 X |
| 4,430,142 | 2/1984 | Ochi et al. | 53/486 X |
| 5,321,935 | 6/1994 | Spatz et al. | 53/75 X |
| 5,400,564 | 3/1995 | Humphries et al. | 53/75 |
| 5,505,572 | 4/1996 | Fujimori | 53/366 X |

*Primary Examiner*—Horace M. Culver
*Attorney, Agent, or Firm*—Loeb & Loeb LLP

[57] ABSTRACT

The invention comprises a DC motor and a mechanism for converting a rotational motion of the DC motor to a linear motion in a vertical direction; a jig driven by the DC motor for performing sealing of a sample container; a DC power source; a section for controlling power supplied from the DC power source to the DC motor; a circuit for detecting a value of current flowing from the DC power source to the DC motor; a section for setting a predetermined load to be applied to the jig when the sample container is sealed by the jig; and a comparator connected to the load setting section and the current value detecting circuit. The comparator compares a target value corresponding to the predetermined load value set in the load setting section, and an actually measured value detected in said current detecting circuit, with each other, and an instruction is issued to the DC motor controlling section when the actually measured value detected by the current detecting circuit exceeds the target value corresponding to the predetermined load value. The instruction controls the jig drive. The arrangement allows the load on the sealer robe accurately controlled without resorting to an expensive load cell or the like.

7 Claims, 4 Drawing Sheets

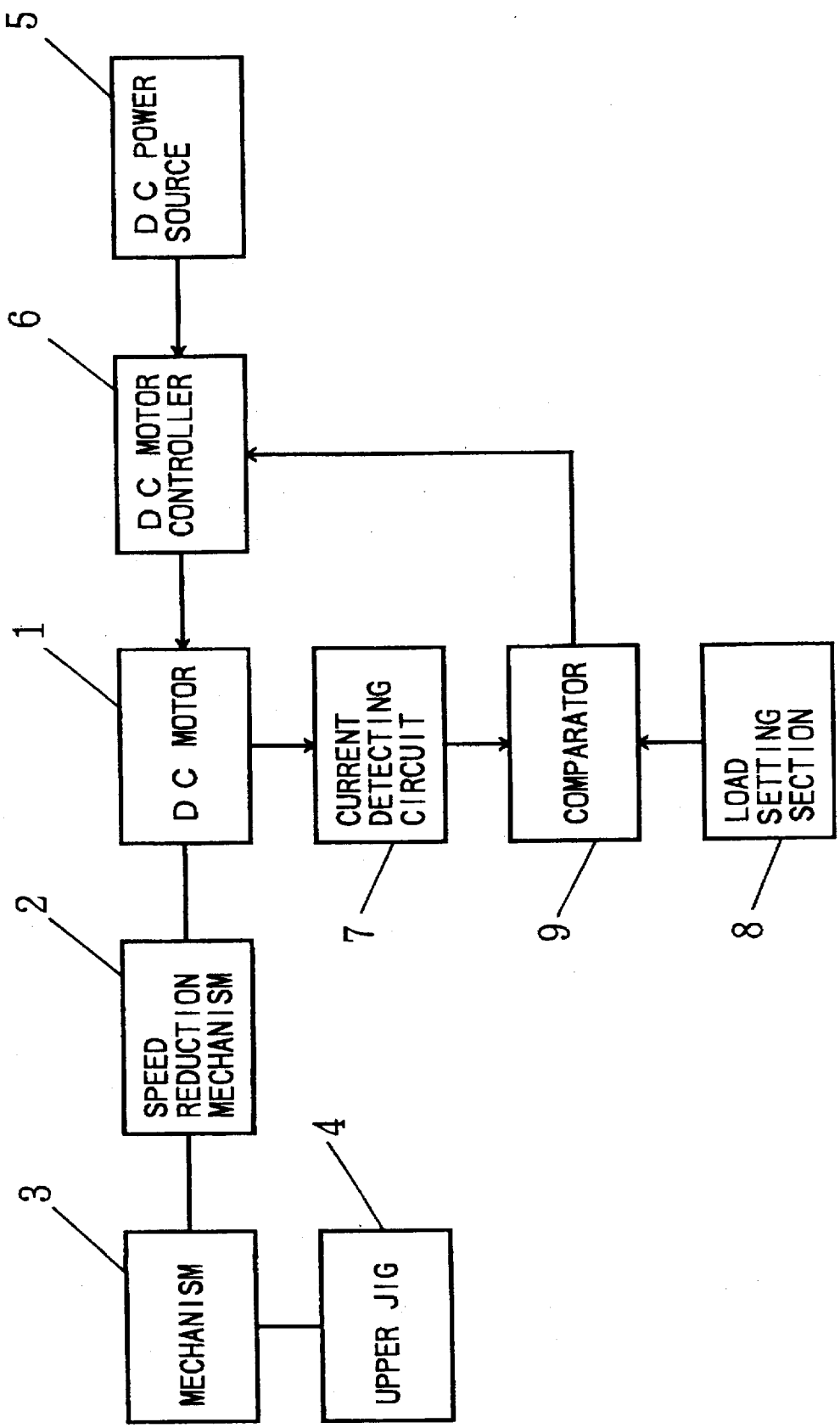

FIG. 2A
FIG. 2B
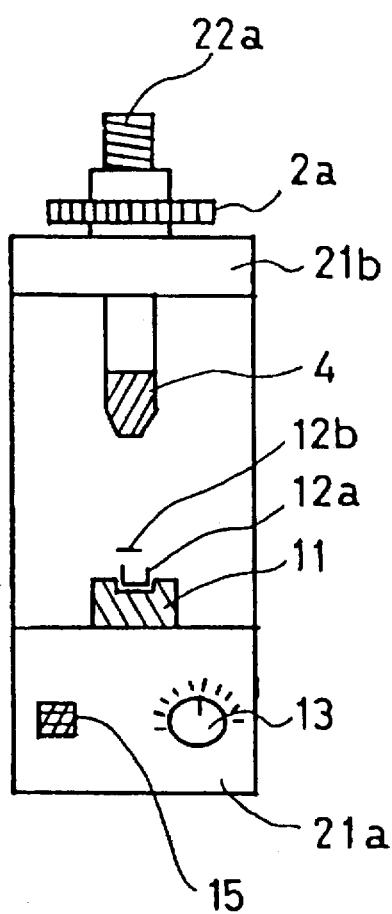
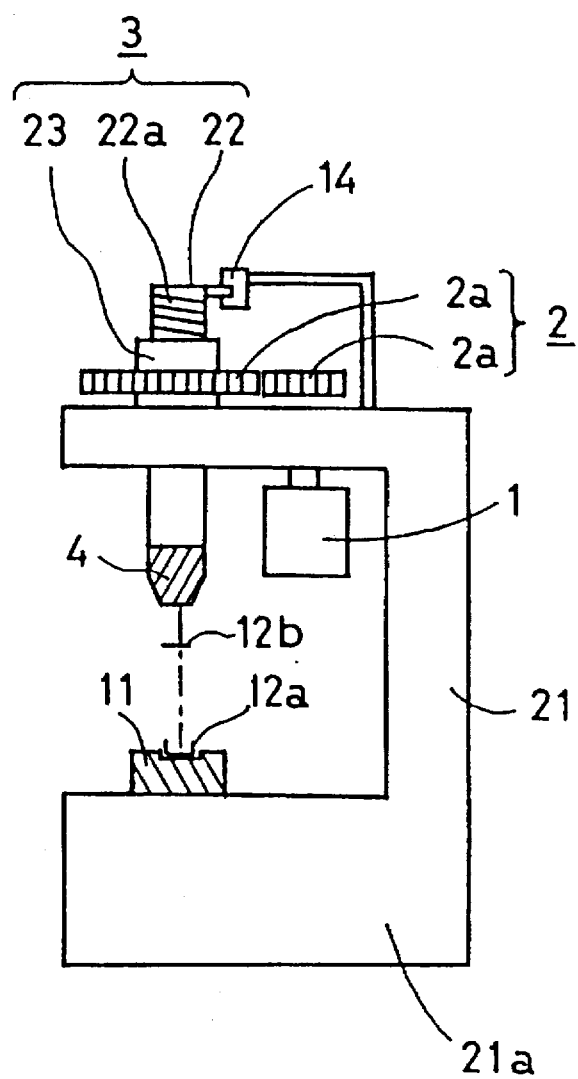

SAMPLE CONTAINER SEALER HAVING FUNCTION OF SETTING LOAD

BACKGROUND OF THE INVENTION

The present invention relates to a sample container sealer for sealing a sample container for use in a thermal analysis apparatus.

A conventional sample container sealer of this type is shown in FIG. 4. A lower jig 11 is detachably mounted at a predetermined position on an upper surface of a bottom arm portion 21a of a U-shaped sample sealer arm 21 by a suitable means (not shown). A recess is provided at a predetermined position of the lower jig 11 for receiving a sample container 12. The sample container 12 is laid in the recess. A pressure shaft 22 which is slidably movable in a direction toward the lower jig 11 is provided on an upper arm portion 21b of the sample sealer arm 21. A male screw 22a is provided around at least part of the pressure shaft. A pressure screw 23 having a female screw thread to be engaged with the male screw 22a is mounted rotatably on the upper portion of the upper arm portion 21b. Furthermore, a lever 20 is provided around the pressure screw 23.

An upper jig 4 is detachably mounted at a lower end (on the side of the lower jig 11) of the pressure shaft 22. The lower jig 11 and the upper jig 4 may be replaced by other ones, respectively, in consideration of a kind of material, a shape and a purpose (sealability) of the sample container 12 to be sealed.

First of all, the sample container 12 to be sealed and the lower jig 11 and the upper jig 4 which are suitable for the purpose of use thereof are set as shown in FIG. 4. A receiver 12a of the sample container 12 on which the sample is laid is set in the recess of the lower jig 11. A container cover 12b is laid thereover. Next, the lever 20 is rotated so that the pressure shaft 22 is slid downwardly. As a result, the receiver 12a of the sample container 12 and the container cover 12b are engaged with each other with some idle play to thereby seal the sample container.

A sealer shown in FIG. 5 will now be explained. In this conventional example, a load cell 22 is provided for measuring a load to be applied to the sample container 12 at a portion of the bottom arm 216 of the sample sealer arm 21 which is to receive the lower jig 11. An output of the load cell 22 is connected to a load indicator 23. The load applied to the seal of the sample container 12 is indicated on the indicator 23.

Sample containers to be used for a thermal analyzing apparatus, particularly for a difference scanning calorimeter (hereinafter referred to as DSC) and a difference thermal analyzer (hereinafter referred to as DTA) generally fall into kinds of an open type, a closed type, a pressure-durable (hermetic) seal type and the like. Also, the material falls into various kinds of aluminum, silver, stainless steel, alumina and the like. These containers are categorized depending upon an object to be measured, a purpose or a temperature range for the measurement. For instance, in the case where the melting of the polymer sample kept in a solid or a powder state is measured, an open type container made of aluminum is generally used. Then, in order to enhance a thermal contact between the sample and the container, a cover is laid on the container, and a treatment for pressing the sample with the cover and the container by rounding or bending (referred to as crimping) an edge of the container is generally carried out. This crimping treatment is carried out with the jigs for the crimping operation being mounted on the sample container sealer.

Also, for example, in the case where the measurement is carried out while preventing the liquid or the like from being gasified for the measurement of the liquid sample, there are cases that the closed type container or the hermetic sealed type container is used depending upon the situation. In this case, the gas-tight closing (sealing) of the sample container which has received the sample therein is carried out under the condition that the respective jigs for the container are mounted on the sample container sealer.

Also, in the case the DSC or the DTA is used for a test methods of self-reacting materials based on Japanese Fire Service Law on Hazardous Materials, a hermetic sealed (pressure-durable gas-tight) container is used.

When the various containers are thus crimped or closed, the containers are treated while applying a suitable load thereto by the jigs. For example, it is preferable that a pressure of 20 to 50 kgW is applied for the crimping operation for the open type container made of aluminum, a pressure of about 200 kgW is applied for the hermetic sealed container made of silver and a pressure of about 300 kgW is applied for the hermetic sealed container made of stainless steel. In the case where a load in sealing is insufficient in the hermetic sealed container, a leakage might occur. Inversely, in the case where it is excessive, the container might be damaged.

Conventionally, in the case where the crimping or sealing operation is carried out by using the manual type sample container sealer as shown in FIG. 4, the suitable lead adjusting methods are, for example, determining the position of the rotary lever 20, or adjustment by depending upon the experience and senses of the operator. Accordingly, there is a disadvantage that the reproduceability of sealing or crimping the container would not be easily attained. Also, a defect in crimping or sealing in the container is liable to occur with the unexperienced operator. Also, the container which needs a large load forces the operator to pull down his or her great physical force. In case of a physically weak operator, there is a disadvantage that there are some cases that the sealing operation would be insufficiently performed.

On the other hand, in the sample container sealer in which the load cell is provided as shown in FIG. 5, the operator carries out the sealing operation or the like while watching the load value measured by the load cell. Accordingly, it would be easy to ensure the reproduceability in comparison with the system which does not use any load cell. Nevertheless, since the operator has to manually carry out the operation, the unexperienced operator is likely to cause defects such as excessive loading. Also, the load cell itself is expensive in comparison with a cost of this type container sealer. Accordingly, there is also a disadvantage that the installation of the load cell increases the cost for the overall container sealer.

Therefore, in order to solve those problems, an object of the present invention is to provide an inexpensive sample container sealer in which a load may be set for sealing with good reproduceability with ease even by an unexperienced operator.

SUMMARY OF THE INVENTION

In order to solve the above-described tasks, according to the present invention, there are provided a DC motor, a mechanism for reducing and converting a rotational motion of said DC motor to a linear motion in a vertical direction, a jig mounted on said mechanism for performing sealing or the like for the sample container, a DC power source, a DC motor controlling section for controlling power supply from said DC power source to said DC motor, a circuit for detecting a value of current flowing from said DC power source to said DC motor, a load setting section for setting in advance a load to be applied to the jig when the sample container is subjected to sealing or the like by said jig, and a comparator connected to said load setting section and said current value detecting circuit for comparing a target value corresponding to the load value set in said load setting section and an actually measured value detected in said current detecting circuit with each other and for issuing an instruction to said DC motor controlling section when the actually measured value detected by said current detecting circuit exceeds the target value corresponding to said load value, whereby the jig is automatically driven by the action of the DC motor, said DC motor is controlled so that a load exceeding the set value is not applied to said jig when said DC motor controlling section receives the instruction from said comparator, and load cell is dispensed with and sealing or the like may be performed at the load which is automatically set.

In the sample container sealer thus constructed, the DC motor controlling section supplies the DC motor with the electric power at the constant voltage in accordance with the operator's instructions, and the DC motor is rotated in accordance with the constant voltage supplied thereto and is used to push down the jig through the mechanism. When the jig abuts against the container set, the jig is lowered intact at the lead corresponding to the torque of the DC motor for performing machining such as crimping or sealing for the container. On the other hand, the lead applied to the jig corresponds to the torque of the DC motor, and the torque of the DC motor corresponds to the value of current flowing through the coils of the DC motor. In the current detecting circuit, the value of current flowing the coils of the DC motor is detected and may output a signal as, for example, a voltage signal, to the comparator. On the other hand, in the lead setting section, the voltage is generated corresponding to the lead value set by the operator and may output a signal as a reference voltage to the comparator. In the comparator, the output voltage from the current detecting section is compared with the reference voltage from the lead setting section through a comparing means. When the output voltage from the current detecting section exceeds the reference voltage, the comparator output the signal to the DC motor controlling section. In the DC motor controlling section, when the signal from the comparator is received, it is judged that the lead applied to the jig exceeds the set lead, the power supply to the DC motor is stopped, or otherwise the voltage which is opposite to the previous one is outputted to release the load from the container.

BRIEF DESCRIPTION OF THE DRAWINGS

FIG. 1 is a block diagram showing the embodiment of the invention.

FIG. 2 is outer schematic views showing the embodiment of the invention, FIG. 2a is a frontal view and FIG. 2b is a side elevational view.

DETAILED DESCRIPTION

Figure 3:
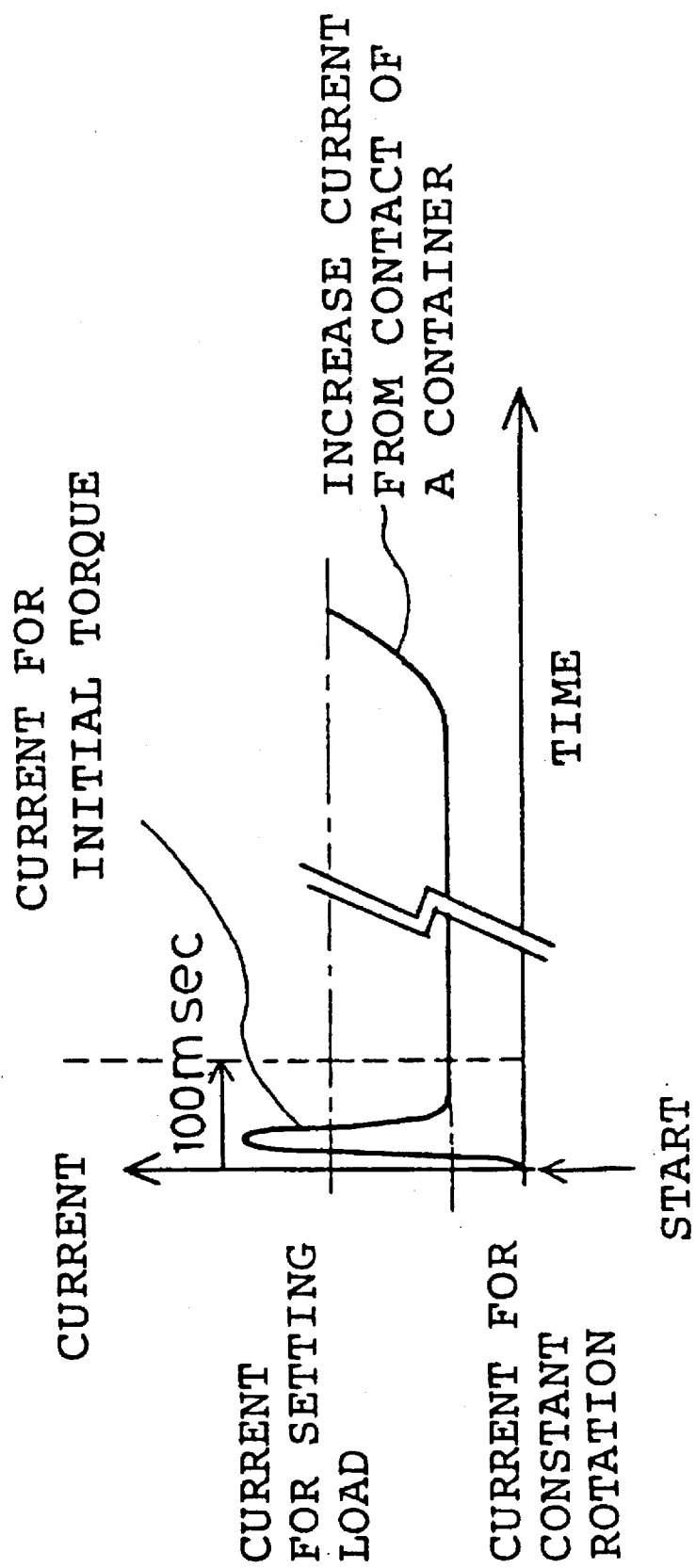
FIG. 3 is a graph showing values of current after the start in accordance with the embodiment of the invention.

An embodiment of the invention will now be explained.

FIG. 1 is a block diagram showing an embodiment of the invention. Numeral 1 denotes a DC motor, numeral 2 denotes a speed reduction mechanism composed of gears for reducing and transmitting a rotation of the DC motor 1, and numeral 3 denotes a mechanism for converting the rotational motion, which has been transmitted through the speed reduction mechanism 2, into a linear reciprocating motion. A jig 4 (upper jig) is mounted at a tip end thereof for carrying out the sealing operation or the like for the sample container.

Numeral 5 denotes a DC power source, and numeral 6 denotes a DC motor controller made of an DC for the motor control for supplying an electric power from the DC power source 5 to the DC Numeral 7 denotes a current detecting circuit for detecting the current which flows through coils of the DC motor. More particularly, in this embodiment, the current detecting circuit is composed of a circuit for detecting, through resistors, the value of the current, as a voltage, flowing a ground of the motor controlling IC of the DC motor controller 6 and amplifying the current with an operational amplifier.

Numeral 8 denotes a load setting section. In this embodiment, the load setting section may part a constant standard voltage with a variable resistor and may output a voltage as a reference voltage for comparison with the voltage outputted from the current detecting circuit 7. The setting of the load is carried out by outputting the reference voltage corresponding to the set load with adjusting the variable resistors. In correspondence between the load and the reference voltage, for example, there are methods in which a relationship between the load and the current value is sought in view of the relationship between the value of the current flowing through the coils and the generated torque from the characteristic diagram of the DC motor and further by calculation of the reduction ratio or the like of the mechanical structure, and in which the relationship is sought by providing a load cell to a position where the sample container is laid and actually measuring the load to be actually measured and the detected current value at that time. Also, of course, the relationship between the current value and the reference voltage is obtained through the calculation with the resistors used in the current detecting section or the amplifying ratio of the amplifier.

Numeral 9 denotes a comparator for comparing the outputs from the current detecting circuit 7 and the load setting section 8 and for issuing the instruction to the DC motor controller 6. In the embodiment, a comparator element for the voltage is used and the input voltage from the load setting section 8 is used as the reference voltage. When the input voltage from the current detecting circuit 7 exceeds the above-described reference voltage, the pulse signal is outputted to the DC motor controller 6. When the pulse signal from the comparator 9 is received in the DC motor controller 6, the voltage which has been supplied to the DC motor 1 so far is immediately reversed, and the DC motor 1 is reversed. Thus, thereafter, any load will not be applied from the jig 4 to the container.

Figure 4:
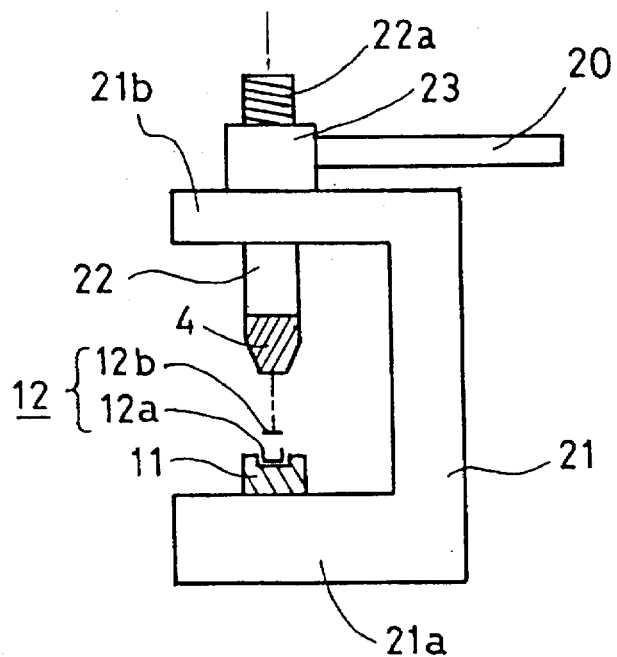
FIG. 4 is an outer schematic view showing a conventional sample container sealer.
Figure 5:
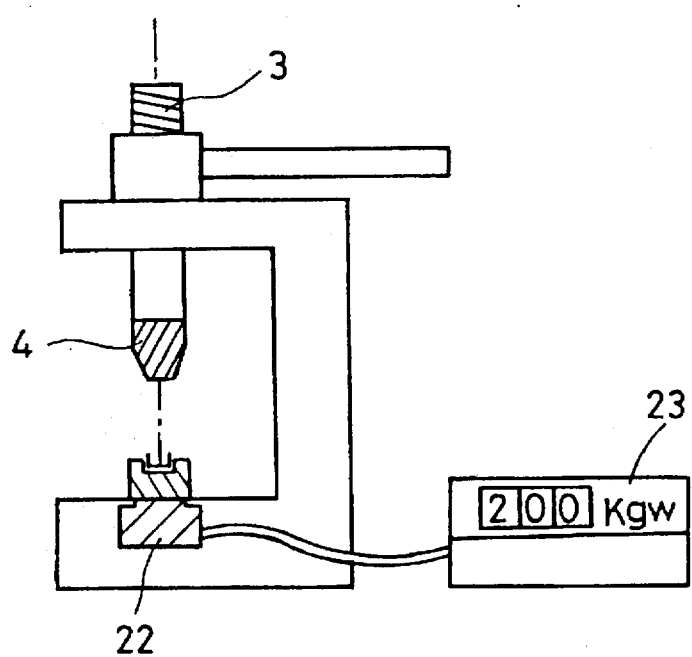
FIG. 5 is an outer schematic view showing a conventional sample container sealer adopting a load cell.

FIG. 2 is outer schematic views showing the sample container sealer in accordance with the embodiment. FIG. 2a is an outer schematic frontal view and FIG. 2b is an outer schematic side elevational view. Numeral 1 denotes a DC motor. Numeral 2 denotes a speed reduction mechanism composed of gears 2a for reducing and transmitting a rotation of the DC motor 1. Numeral 3 denotes a mechanism for converting the rotational motion, which has been reduced and transmitted through the speed reduction mechanism 2, into a linear reciprocating motion. Same as shown in FIG. 4, converting (the speed reduction) mechanism is provided with a pressure shaft 22 having a male screw 22a at its part and a pressure screw 23 having a female screw which is engaged with the male screw 22a. The pressure screw 23 is mounted rotatably on the upper portion of an upper arm portion 21b.

A Jig 4 (upper Jig) is mounted at a tip end of the mechanism 3. Numeral 21 denotes an arm for supporting the DC motor 1, the speed reduction mechanism 2, the mechanism 3 and the like. At the same time, furthermore, an electric circuit section such as a DC power source 5, a DC motor controller 6 and the like is disposed in the arm.

Numeral 11 denotes a lower Jig which forms a pair with an upper jig 4. A receiver 12a and its cove 12b of the sample container 12 in which the sample is laid are provided on the lower jig. The upper jig 4 is lowered from above by the rotation of the DC motor 6. The crimping or sealing of the sample container 12 is carried out by applying a load on the cover 12b of the sample container 12 or an outer peripheral portion of the sample container 12. The jig 4 and the lower jig 11 may be replaced by other ones depending upon the container to be used.

Numeral 13 denotes a knob of a variable resistor of the load setting portion 8 for setting the load to be applied to the jig 4. A scale is applied to a position of the knob 13 corresponding to a predetermined load.

Numeral 14 denotes a position detector such as a microswitch, a photo sensor or the like for detecting whether the jig 4 or the pressure shaft 22 is located at the upper predetermined position. In the embodiment, the position detected by the position detector 14 is set at an initial position. In the case where the sample container 12 is set and the jigs 4 are replaced, the mechanism 3 including the jig 4 is stopped at this initial position.

Numeral 15 denotes a start switch for stating the drive of the DC motor. A pulse is give to the IC of the DC motor controller 6 by depressing this switch. A constant voltage is supplied to the DC motor 1 in the DC motor controller 8. The jig 4 is moved downwardly through the speed reduction mechanism 2 and the mechanism 3 to thereby apply an external force to the sample container 12.

Incidentally in the embodiment, during a period of 100 msec after the start switch 15 has been depressed to give the pulse to the DC motor controller, even if the current value of the DC motor in the comparator exceeds the set target value, the instruction signal is not issued to the DC motor controller. The reason for this is, as shown in FIG. 3, that an initial torque is needed due to the inertia for the short period immediately after he supply of current to the DC motor until the normal rotational speed, and there is a possibility that the current value corresponding to the set load would be exceeded during this period. Accordingly, for the period (about 100 msec in the embodiment) until the DC motor 1 reaches the constant rotational speed, an approach for issuing no instruction signal in the comparator 9 is taken. Incidentally, in the embodiment, the instruction signal output from the comparator 9 is interrupted. However, a method in which the current detection itself is not carried out or a method in which the instruction signal is disregarded in the DC motor controller even if it receives the instruction signal may be adopted.

The operation in the case where the sample container 12 is crimped in accordance with the embodiment will be explained.

The operator introduces the sample to be measured in the receiver 12a of the sample container 12 and covers it by the cover 12b.

Next, the container 12 in which the sample has been Introduced is laid on the lower jig 11.

Next, the load setting knob 13 is set in the range of load of 20 kgW to 50 kgW suitable to the crimp.

Next, when the start switch 15 As depressed, the upper jig 4 begins downward movement. When the upper jig 4 abuts against the sample container 12 and starts crimp, a load needed for crimp of the sample container 12 is applied to the DC motor 1 through the jig 4, the mechanism 3 and the speed reduction mechanism 2. Corresponding to this, the rotational speed starts to decrease. As a result, a value of current flowing through the coils of the DC motor 1 starts to increase. Since the increment of the current is in proportion to the increment of the torque of the DC motor, finally, the load to be imposed on the sample container 12 through the jig 4 corresponds to the increment of the current of the DC motor. On the other hand, in the comparator 9, the value of current (voltage value) outputted from the current detecting circuit 7 and the reference voltage value corresponding to the load set in the load setting section 8 are continuously compared with each other. When the load is increased to exceed the set load while the jig 4 abuts against the sample container 12 for crimp, in the comparator 9, the value of current (voltage value) from the current detecting circuit 7 exceeds the reference voltage value corresponding to the load set in the load setting section 8 so that the pulse Of the instruction signal is outputted to the DC motor controller 6. In correspondence with the pulse, in the DC motor controller 6, a constant voltage which is in the opposite direction to the previous one is supplied to the DC motor 1 by the DC motor controlling 1C. As a result, the upper jig 4 starts to move upwardly and the sample container 12 is left in the condition that it is crimped by the lower jig 11.

When the upper jig 4 is moved upwardly to the initial position, the position detector 14 operates to output the signal (pulse) to the DC motor controller 6. The DC motor controller 6 receives this signal and stops the power supply to the DC motor 1 by the DC motor controlling 1C so that the jig 4 is stopped at the initial position.

After the jig 4 has been stopped at the initial position, the operator picks up the sample container 12 crimped at the set load.

As is apparent from the series of operations, although the crimp of the container is conventionally carried out while manually rotating the lever 20 and applying the load by the operator's sense, if the sample container sealer in accordance with the embodiment of the invention is used, the operator installs the sample container onto the lower jig 11 and only depresses the start switch 15 to thereby perform the crimp of the sample container at the suitably set load.
[0027]

Accordingly, in the conventional manner, the crimp condition of the container or the sealing condition thereof is varied by the force adjustment of the operator, and in case of the unaccustomed operator, the failure might frequently occur. However, if the sample container sealer in accordance with the embodiment of the invention, the crimping and sealing may be automatically carried out irrespective of the operator. Accordingly, even the unaccustomed operator may carry out the crimping and sealing with high reproduceability without fail.

Also, even in the sealing operation of the hermetic seal (closed type) container which needs a high load, only by replacing the jigs 4 and the lower jigs 11, setting the load value of 200 kgW to 300 kgW by using the knob 13 and simply pushing the start switch 15, the operator may carry out the sealing operation without fail and without any particularly large force. Furthermore, as is apparent from the embodiment, with the structure in which the movement of the jig is carried out by the DC motor and at the same time, the load applied to the jig due to the increment of the torque applied to the DC motor is limited, it is obvious that the crimping and sealing may be carried out at the suitable load with the good reproduceability even without using the expensive load cell.

In the embodiment, the comparator 9 and the load setting section 8 are shown as simple analog circuits which are formed, in combination, of the voltage comparator element, the standard voltage and the variable resistor. However, for example, it is possible to form the system so that the comparator 9 has a CPU the input of the set load of the load setting section 8 is digitalized, and the input from the current detecting circuit 7 is converted into a digital value with an A/D converter for comparison in digital value.

With such an arrangement, a means for identifying the jigs is provided in the jig 4 and the lower jig 11 by an electric contact or the like having about 2 bits and the 2 bit signal is given to the CPU of the comparator 9 in replacement and installation of the jigs and the CPU may automatically set the set load value corresponding to the set jigs. With such an arrangement, it is possible to automatically carry out the crimping and sealing at the suitable load even if the operator does not necessarily set the load. Also, in case of this structure, for example, even in the case where the tendency of increment of the load applied to the jig 4 in the crimping operation is not the simple increment but that having a peak or the like on the way, by storing a change pattern of the corresponding current value in the memory, it is possible to more suitably set the load for the container.

Also, in the embodiment, the system of the current detecting circuit 7 is adopted for performing the detection from the ground current of the DC motor controlling IC. However, any other means may be obviously used if it detects the value of the current flowing the coils of the DC motor 1.

Namely, the sample container sealer for carrying out the crimp operation of the sample container in which the sample is received for the thermal analysis according to the present invention is comprised of the jigs (upper jig 4 and lower jig 11) for crimping the sample container, the drive means (speed reduction mechanism 2 and the mechanism 3) including the DC motor 1 for driving the above-described jigs, the DC motor controller 6 for controlling the power supply to the above-described DC motor 1, and the load detecting means (current detecting circuit 7) for detecting the load to be applied to the above-described sample container 12 from the value of the current flowing through the coils of the above-described motor 1. The DC motor 1 is controlled by the detected load. As a result, the crimp operation of the sample container 12 may be carried out at the predetermined load.

As described above, in the sample container sealer according to the present invention, the drive of the jigs for crimping or sealing the sample container is automatically carried out by the DC motor, and at the same time, the load to be applied to the jig is detected from the value of current flowing through the DC motor so that at the time the predetermined load value is exceeded, the drive of the jigs by the DC motor is controlled in the direction in which the load is not applied to the container. Accordingly, it is possible to ensure the effect in which the crimping or sealing of the sample container may readily be carried cue with good reproduceability.

Also, since it is possible to seal the closed type container, which needs a large load, with such a force that the start switch is depressed, for example, the female operator who has no strong force does not pull down her force, for sealing with good reproduceability.

Furthermore, even if a relatively expensive load cell is not adopted, the load may readily be set for the crimping and sealing. Accordingly, it is advantageous to provide an inexpensive sample container sealer of this type.

Furthermore, by using the CPU in the comparator and causing the jigs to have the identifying means, the crimping and sealing may be carried out at the suitable load without necessity to pay any attention to the difference in containers or jigs.

What is claimed is:

1. In a sample container sealer for carrying out crimp of a sample container in which a sample is received for thermal analysis, a sample container sealer having a function to set a load, characterized by comprising a DC motor, a mechanism for reducing and converting a rotational motion of said DC motor to a linear motion in a vertical direction, a jig mounted on said mechanism for crimping the sample container, a DC power source, a DC motor controlling section for controlling power supply from said DC power source to said DC motor, a circuit for detecting a value of current flowing from said DC power source to said DC motor, a load setting section for setting in advance a load to be applied to the jig when the sample container is crimped by said jig, and a comparator connected to said load setting section and said current value detecting circuit for comparing a target value corresponding to the load value set in said load setting section and an actually measured value detected in said current detecting circuit with each other and for issuing an instruction to said DC motor controlling section when the actually measured value detected by said current detecting circuit exceeds the target value corresponding to said load value, wherein said DC motor is controlled so that a load exceeding the set value is not applied to said jig when said DC motor controlling section receives the instruction from said comparator, thereby crimping the sample container by the load set in advance.

2. The sample container sealer having a function to set a load according to claim 1, wherein a position detector is provided for detecting whether a position of the jig mounted on the mechanism for converting the motion to the linear motion in the vertical direction is the position in which a sufficient space is kept for installing the sample container, and wherein when the instruction is issued from said comparator, said jig is controlled to be moved in a direction away from the sample container in said DC motor controlling section, and when the position of said jig reaches a position in which it is detected by said position detector, the movement of said jig is stopped.

3. The sample container sealer having a function to set a load according to claim 1, wherein a start means for starting the movement of the jig is provided in the DC motor controlling section and in order for said start means to disregard an initial torque of the DC motor immediately after the movement of the jig has been started, a current detection is not carried out for a constant period of time after the start of the movement, or any instruction signal is not issued from the comparator to said DC motor controlling section, or the instruction signal is disregarded in the DC motor controlling section.

4. The sample container sealer having a function to set a load according to claim 2, wherein a start means for stating the movement of the jig is provided and the DC motor controlling section is provided for supplying a constant voltage to said DC motor after the start of the movement, and supplying a constant voltage which is opposite to the previously mentioned constant voltage to said DC motor after the instruction is issued from the comparator.

5. The sample container sealer having a function to set a load according to claim 1, wherein the comparator has a CPU and is constructed to be supplied as an input with the load value in terms of digital values from the load setting section and to convert the output from the current detecting circuit into the digital values through an A/D converter, and said comparator compares the digital values with each other.

6. The sample container sealer having a function to set a load according to claim 5, wherein a means for identifying a kind of the jig in replacement of jigs is provided, a signal of said identifying means is transmitted to the CPU of the comparator, and the value of the set load is determined on the basis of the signal of said jig identifying means in said comparator.

7. In a sample container sealer for carrying out crimp or seal of a sample container in which a sample is received for thermal analysis, a sample container sealer having a function to set a load, characterized by comprising a jig for crimping or sealing the sample container, a drive means including a DC motor for driving said jig, a DC motor controlling section for controlling electric power supply to said DC motor, and a load detecting means for detecting a load to be applied to said sample container from a value of current flowing coils of said DC motor, wherein said DC motor is controlled from said detected load so that the crimp or seal of the sample container may be carried out at a predetermined load.

* * * * *